United States Patent [19]
Palombo et al.

[11] Patent Number: 5,805,279
[45] Date of Patent: Sep. 8, 1998

[54] METHOD AND APPARATUS FOR ILLUMINATING AND IMAGING A CAN END COATED WITH SEALING MATERIAL

[75] Inventors: Thomas H. Palombo, Akron; Gareth O. Ridout, Ravenna, both of Ohio

[73] Assignee: Alltrista Corporation, Muncie, Ind.

[21] Appl. No.: 584,615

[22] Filed: Jan. 11, 1996

[51] Int. Cl.⁶ .................................................. G01N 21/00
[52] U.S. Cl. .......................................................... 356/240
[58] Field of Search .................................... 356/201, 240; 250/223 B, 338, 341; 209/111.7

[56] References Cited

U.S. PATENT DOCUMENTS

| 2,798,605 | 7/1957 | Richards . | |
|---|---|---|---|
| 3,639,067 | 2/1972 | Stephens | 356/240 |
| 3,687,559 | 8/1972 | Fischer | 356/240 |
| 3,886,356 | 5/1975 | Gomm | 250/223 |
| 3,894,806 | 7/1975 | Remy et al. | 356/240 |
| 4,017,194 | 4/1977 | Conroy et al. | 356/240 |
| 4,025,201 | 5/1977 | Deane | 356/240 |
| 4,026,414 | 5/1977 | Ellinger | 209/111 |
| 4,026,656 | 5/1977 | Kusz et al. | 356/51 |
| 4,262,196 | 4/1981 | Smith | 250/223 |
| 4,280,624 | 7/1981 | Ford | 209/524 |
| 4,293,219 | 10/1981 | Ducloux | 356/240 |
| 4,376,951 | 3/1983 | Miyazawa | 358/106 |
| 4,424,411 | 1/1984 | Bieringer et al. | 250/223 |
| 4,428,674 | 1/1984 | Giebel et al. | 356/240 |
| 4,435,641 | 3/1984 | Hajime | 250/223 |
| 4,448,526 | 5/1984 | Miyazawa | 356/237 |
| 4,459,023 | 7/1984 | Reich et al. | 356/237 |
| 4,491,728 | 1/1985 | Fischer | 250/223 |
| 4,498,003 | 2/1985 | Cibis | 250/223 |
| 4,546,247 | 10/1985 | Peyton et al. | 250/223 |
| 4,580,045 | 4/1986 | Kulig | 250/223 |
| 4,606,635 | 8/1986 | Miyazawa et al. | 356/240 |
| 4,650,326 | 3/1987 | Nagamine et al. | 356/240 |
| 4,668,983 | 5/1987 | Werson | 358/106 |
| 4,680,463 | 7/1987 | Lutgendorf et al. | 250/223 |
| 4,691,231 | 9/1987 | Fitzmorris et al. | 358/106 |
| 4,731,649 | 3/1988 | Chang et al. | 358/106 |
| 4,758,084 | 7/1988 | Tokumi et al. | 356/237 |
| 4,760,270 | 7/1988 | Miller | 250/563 |
| 4,865,447 | 9/1989 | Shay | 356/240 |
| 4,882,498 | 11/1989 | Cochran et al. | 250/571 |
| 4,912,318 | 3/1990 | Kajiura | 250/223 |
| 4,914,289 | 4/1990 | Nguyen et al. | 250/223 |
| 4,924,107 | 5/1990 | Tucker | 250/572 |
| 4,972,093 | 11/1990 | Cochran et al. | 250/572 |
| 5,051,825 | 9/1991 | Cochran et al. | 358/106 |
| 5,072,127 | 12/1991 | Cochran et al. | 250/572 |
| 5,095,204 | 3/1992 | Novini | 250/223 |
| 5,132,791 | 7/1992 | Wertz et al. | 358/106 |
| 5,167,157 | 12/1992 | Wertz et al. | 73/627 |
| 5,172,005 | 12/1992 | Cochran et al. | 250/57 |
| 5,187,611 | 2/1993 | White et al. | 359/599 |
| 5,216,481 | 6/1993 | Minato | 356/240 |
| 5,247,344 | 9/1993 | Doan | 356/394 |
| 5,249,034 | 9/1993 | Minato | 356/375 |
| 5,331,151 | 7/1994 | Cochran et al. | 250/223 |

Primary Examiner—Frank G. Font
Assistant Examiner—Michael P. Stafira
Attorney, Agent, or Firm—Brinks Hofer Gilson & Lione

[57] ABSTRACT

A can end to be inspected, including a portion coated by a sealing material, is illuminated by polarized light. The light reflected from the object and sealing material is viewed by a camera through a polarizing filter. The polarizing filter blocks out polarized light reflected by the can end and sealing material that does not contain any defects, but passes light reflected by the sealing material that has been depolarized by a defect in the sealing material.

16 Claims, 5 Drawing Sheets

METHOD AND APPARATUS FOR ILLUMINATING AND IMAGING A CAN END COATED WITH SEALING MATERIAL

The present invention relates to illuminating and imaging can ends that are at least partially coated with sealing material, and particularly to methods and apparatus for detecting defects in the sealing material. More particularly, the invention relates to the use of polarized light to enhance the image of a defect in the sealing material.

BACKGROUND OF THE INVENTION

Manually operated can end openings are known. Such can ends are primarily used to close containers of carbonated beverages, such as beer and soft drinks against internal pressures that can exceed 90 psi. Such can end openings typically include a gate defined by a scoring cut into the inside of the can end that provides a weakened perimeter around the gate. As a force is applied to the gate, the weakened perimeter tears, allowing the gate to be pushed inwardly or pulled outwardly to provide the can end opening. Typically, the gate is actuated by pull tabs or push-in tabs or the now common lever-operated push-in tab.

To minimize the force required to tear the scoring, the can end is scored substantially to the thickness of the can end metal. Because of variations in the thickness of can end metal and in the scoring process, it is possible for the scoring tool to penetrate entirely through can ends being manufactured and result in can ends that will not contain the high internal pressure of a carbonated beverage can. To protect against the loss of carbonation and the unwanted entry of air into containers closed with such can ends, a sealing material is applied over the scoring on the underside of the can end.

Since the integrity of the seal provided by the can end and the sealed scoring is necessary to protect and preserve the carbonation of a can's contents, the sealing material applied to the can ends must be checked to ensure the absence of defects. Such defects can take the form of gaps or bubbles formed in the sealing material which either fail to cover a portion of the scoring or provide limited coverage which can be breached. Preferred can end sealing materials are usually transparent, and conventional vision inspection systems are unable to reliably detect defects in such transparent sealing materials. Hence, inspection of can ends for defects in the scoreline sealing material poses a problem.

Adding to the problem of inspecting can ends is the fact that, typically, a varnish-like coating is applied to the entire can end and a second type of sealing material is applied near the perimeter of the can end to seal the can end to the can body. Having a different purpose, this second sealing material has different properties, and consequently requires different inspection techniques. Thus, a vision inspection system must be capable of detecting defects in both types of sealing materials, preferably without requiring an additional expensive inspection station and without using additional cameras and the like.

SUMMARY OF THE INVENTION

The present invention provides a method and apparatus for illuminating and imaging a can end that is at least partially covered with a sealing material. The apparatus comprises a light source for illuminating the can end, means for polarizing the light from the light source, imaging means for receiving light reflected from the can end, and a polarizing filter. The polarizing filter is positioned between the can end and the imaging means and increases the contrast between light passing through the sealing material and light reflected from portions of the can end that have been thinly covered or remain uncovered with sealing material. By increasing the contrast between light passing through the sealing material and light reflected from uncovered or thinly covered portions of the can end, the invention enhances the image of defects, such as gaps, in the sealing material.

In preferred embodiments of the invention, the imaging means includes a camera and the light source includes a circular fluorescent light centered on the optical axis of the camera. A sheet of polarizing material is positioned so that only polarized light reaches the can end to be inspected. The polarizing filter is oriented, relative to the polarizing material, to block the polarized light that is reflected to the camera from portions of the can end that have little or no sealing material. Additionally, the polarizing filter is positioned relative to the camera so that only light reflected from the central portion of the can end with the scoring passes through the filter to the camera. In most can ends, the central portions include an uncovered area enclosed by the covered scoreline portion to reduce the amount of sealing material required, thereby reducing costs.

The invention also includes a method for illuminating and imaging a can end having at least a portion thereof coated with a sealing material. The method includes the steps of locating a camera and a polarizing filter at an inspection station, conveying the coated can end to an inspection station, illuminating the can end with polarized light, and passing reflected light through the polarizing filter to the camera, the polarizing filter being oriented to prevent reflected polarized light from being received by the camera.

In preferred embodiments, the camera is positioned so that the entire can end is within the field of view of the camera. The polarizing filter is positioned relative to the camera so that only light reflected from the covered portion being inspected is received by the camera through the polarizing filter.

The invention provides a method and apparatus for inspecting coating material for defects. Further, the invention permits a single camera to inspect the coated portion of the can end, using the polarizing filter to enhance the image of any defects in the sealing material, and simultaneously inspect the remainder of the can end.

Additional features and advantages of the invention will become apparent to those skilled in the art upon consideration of the following detailed description of a preferred embodiment exemplifying the best mode currently known of carrying out the invention.

DETAILED DESCRIPTION OF THE DRAWINGS

Figure 1:
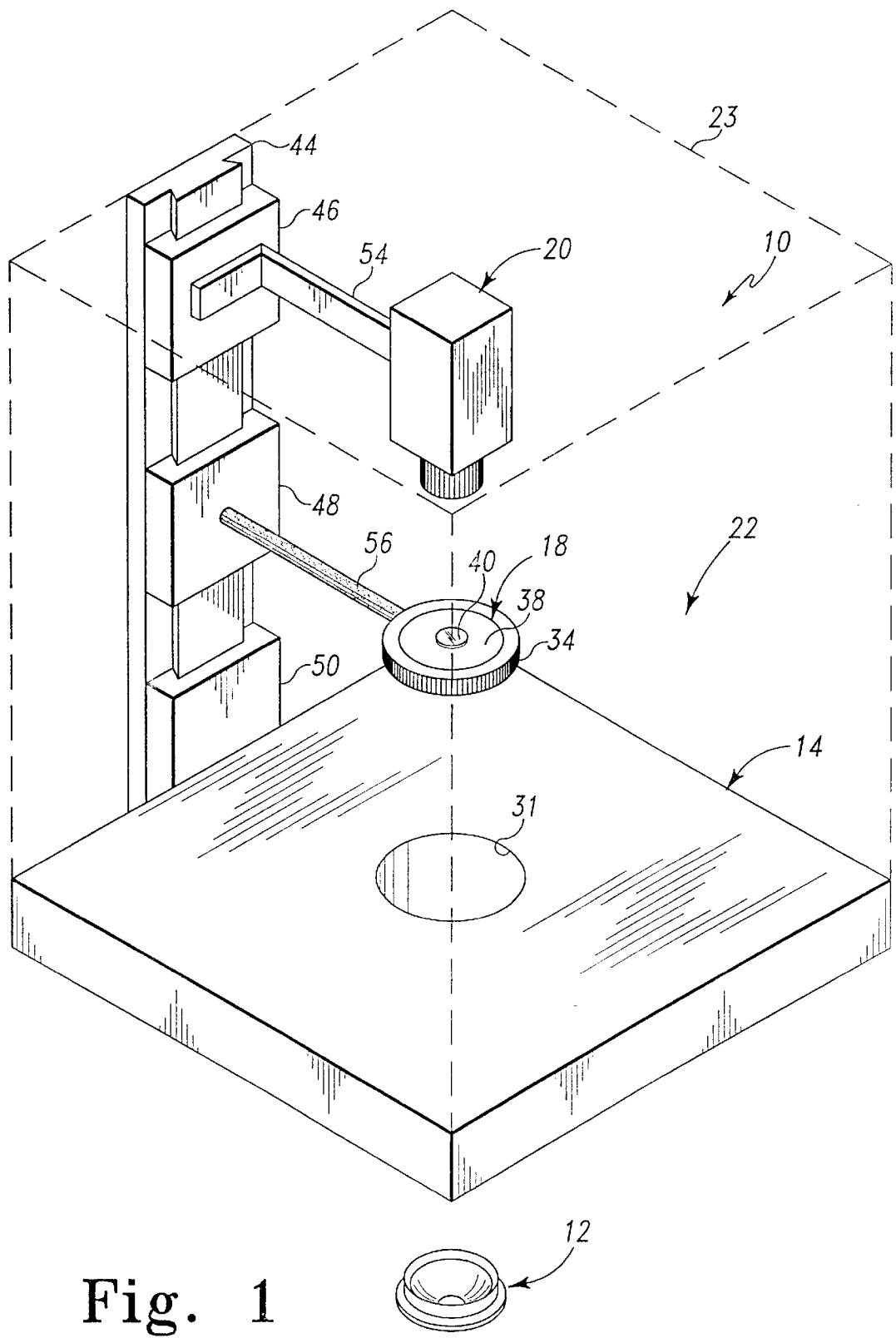
FIG. 1 is a perspective view of a presently preferred embodiment of the invention.

An apparatus 10 for illuminating and imaging a can end 12 is illustrated in FIG. 1. The apparatus 10 includes a light source 14, polarizing means 16 (FIG. 2) for polarizing the light from the light source 14, an analyzer 18, and imaging means 20 for receiving a reflected image of the can end 12. The light source 14, polarizing means 16, analyzer 18 and the imaging means 20 are positioned at an inspection station 22. In preferred embodiments, the light source 14, polarizing means 16, analyzer 18 and imaging means 20 are enclosed within an optics enclosure 23 (shown in phantom) to prevent ambient light from reaching the imaging means 20 and to protect the equipment from contamination due to the workplace environment.

Figure 2:
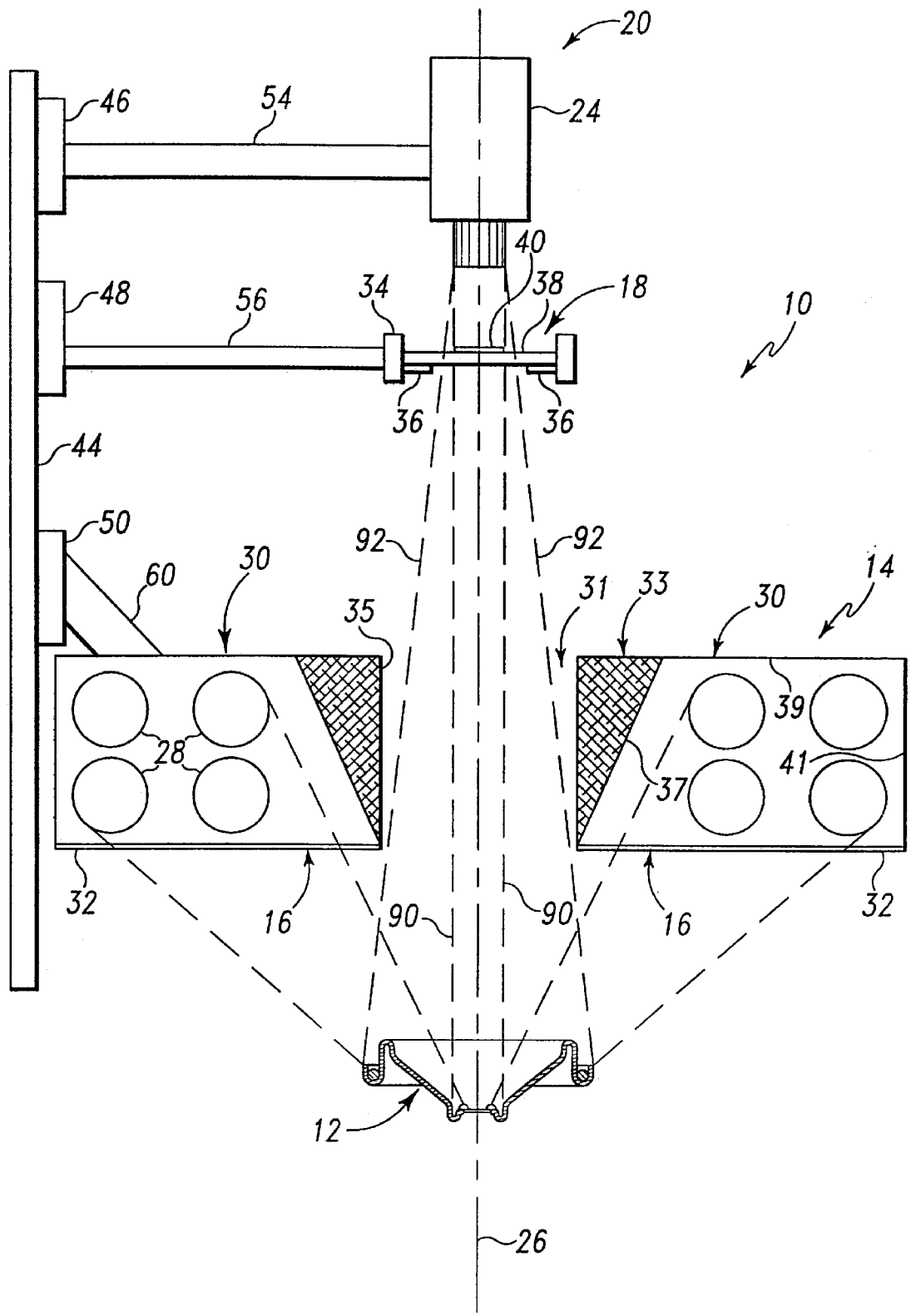
FIG. 2 is a side view of the embodiment of FIG. 1.

The imaging means 20 includes a camera 24, such as a conventional solid state camera device that captures an image on a MOS pixel array, that is positioned so that its optical axis 26 generally passes through the center of the can end 12 located at the inspection station 22. As illustrated in FIG. 2, the camera 24 is located, relative to the can end 12, so that the field of view of the camera 24 includes the entire can end 12.

The light source 14 is positioned to illuminate the can end 12 at the inspection station 22, and can include any conventional light source, but preferably includes a circular fluorescent light 28 mounted in a light fixture 30. As more clearly illustrated in FIG. 2, the light fixture 30 includes a central aperture 31 centered about the optical axis 26 of the camera 24, and an aluminum conical center piece 33 disposed in the central aperture 31 to block unpolarized light from reaching the camera 24 directly from the fluorescent light 28. A central bore 35 is formed in the conical center piece 33 to provide a path for light reflected from the can end 12 to reach the camera 24. The outer surface 37 of the conical center piece 33 is polished to provide a reflective surface to increase the amount of light reaching the can end 12 from light 28. Additional reflective surfaces are provided by applying aluminized mylar film to the inside surfaces 39 and 41 of the light fixture 30. The polarizing means 16 includes a polarizing sheet 32 sized and configured to cover the bottom of the fixture 30 to prevent non-polarized light from illuminating the can end 12.

The analyzer 18 is disposed between the camera 24 and the can end 12 so that reflected light from the can end 12 passes through the analyzer 18 before being received by the camera 24. In preferred embodiments, the analyzer 18 is mounted in a circular holding ring 34 having a plurality of holding pins 36 extending radially inwardly from the ring 34 and includes a circular sheet of glass 38 positioned on the pins 36 and extending outwardly to the ring 34. A polarizing filter 40, comprising a small circular piece of polarizing material, is glued or otherwise attached to the center of the glass 38. The analyzer 18 can be rotated inside the ring 34 to orient the polarizing filter 40 relative to the polarizing sheet 32.

The apparatus 10 also includes a dovetail slide bar 44 which is configured to slidably engage a plurality of dovetail slide members 46, 48 and 50. The slide bar 44 and slide members 46, 48 and 50 cooperate to provide means for adjusting the positions of the camera 24, analyzer 18 and light fixture 30 relative to each other and relative to the can end 12 to be inspected. It will be appreciated that any conventional apparatus for allowing relative positioning of the components of the system, such as a circular rod configured to engage a plurality of circular rings, can be used without departing from the scope of the invention.

The dovetail slide bar 44 is rigidly attached to the inspection station 22 by conventional means. The camera 24 is attached to slide member 46 by bracket 54, the analyzer 18 is attached to slide member 48 by connecting rod 56, and the light fixture 30 is attached to slide member 50 by connecting member 60. Each slide member 46, 48 and 50 incorporates a tightening screw (not shown) to lock the slide member 46, 48, 50 in place once the camera 24, analyzer 18 and light fixture 30, respectively, are properly positioned.

Figure 3:
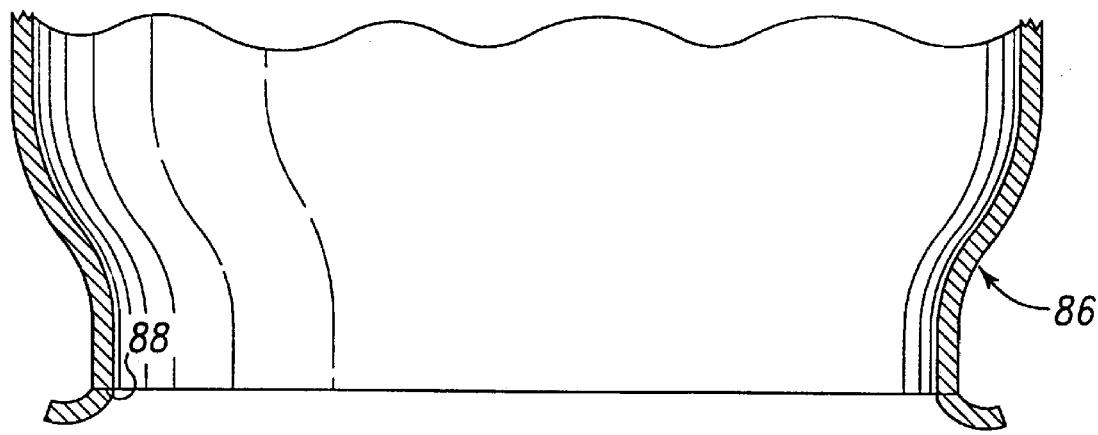
FIG. 3 is a section view of a can top and can body, shown inverted, prior to being joined together.
Figure 3:
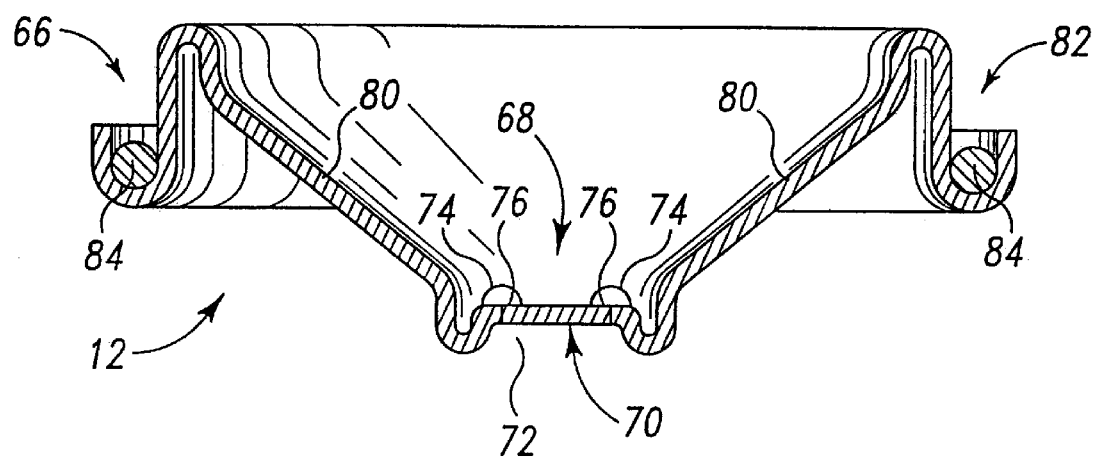

In operation, a can end 12 to be illuminated and imaged, illustratively a can end for a beverage can, is conveyed to the inspection station 22 in a conventional manner. As shown illustratively in FIG. 3, one type of can end 12 to be inspected includes a peripheral portion 66 and a central portion 68. The central portion 68 includes a gate 70 defined by a generally circular interrupted scoring 72. A bead of conventional sealing material 74 is disposed along the scoring 72 so as to seal the scoring 72 and covers an area 76 of the can end 12 immediately adjacent the scoring 72. The entire central portion 68 of the can end 12 can be covered with the sealing material 74, but preferably the sealing material 74 forms an annular ring around a center area 80 in order to reduce the amount of sealing material 74 used, thereby saving production costs. It will be appreciated that the gate can be formed anywhere on the can end, and is not restricted to the central portion 68. The present invention is capable of inspecting the sealing material 74 without regard to its location on the can end 12.

The peripheral portion 66 includes a J-shaped channel 82 extending around the circumference of the can end 12. The J-shaped channel 82 is formed by the peripheral curl of the can end used to attach it to a can body. A second sealing material 84 is disposed in the J-shaped channel 82 to seal the can end 12 to a can body 86. The top end 88 of the can body 86 is pushed into the J-shaped channel 82, and the end 88 of the can 86 and peripheral curl of the can end are double-seamed together in a manner well known in the art. In the double-seaming operation, the second sealing material 84 is squeezed between the can end and the can body, sealing the interface between can end 12 and the can body 86.

The second sealing material 84, having a different function than the first sealing material 74, can have different light diffusion and reflection characteristics. For example, the first sealing material 74 may be transparent while the second sealing material 84 may be black and opaque. This can happen when each sealing material is FDA approved for one function, i.e., sealing the gate or the can end/can body connection, but not the other. Accordingly, a visual inspection system that reliably detects defects in the first sealing material 74 may by unable to reliably detect defects in the second sealing material 84, and vice versa. The present invention eliminates that shortcoming by allowing the simultaneous visual inspection of the first sealing material 74 and the second sealing material 84 by a single imaging means 20. Moreover, the present invention is effective whether or not the can end is coated with a varnish-like coating, as is typical of conventional can ends.

Once positioned at the inspection station 22, the entire can end 12 is illuminated with polarized light from the light source 14. The can end 12 specularly reflects the polarized light. That is, the polarization is retained. The sealing material 74, on the other hand, diffusely reflects the light whereby the polarization is randomized (depolarized). Thus, a smaller percentage of the light reflected from the sealing material 74 retains the polarization and thereby contrasts with the can end 12. The invention takes advantage of this contrast to differentiate between light that is affected by sealing material 74 in the covered area 76 and light reflected from the uncoated areas 80.

If the sealing material 74 contains a defect, such as a gap in the material that leaves a portion of the can end 12 uncovered, the light reflected from the gap will remain polarized and will be blocked out by the polarizing filter 40, while the depolarized light from the sealing material 74 is passed through the polarizing filter 40 to the camera 24. Accordingly, the defect (gap) shows up as a dark area in the midst of the lighter covered area 76.

If the defect is a bubble in the sealing material 74, the light will be depolarized to a lesser extent than the light reflected from the surrounding areas. Therefore, a bubble will show up as a somewhat darker area, with the degree of darkness depending on the size of the bubble. Thus, the invention permits differentiation between reflected polarized light from the uncovered areas 80 and depolarized light reflected from sealing material 74.

In preferred embodiments of the invention, the polarizing filter 40 is sized and positioned to block all polarized light that is reflected from a covered area 76 of the can end 12, including light reflected from any uncovered area 80 surrounded by the bead of sealing material 74, while allowing light reflected from the remaining uncovered areas 80 of the can end 12 to reach the camera 24 unaffected. Thus, light rays 90 from the covered area 76 must pass through the polarizing filter 40 to reach the camera 24, whereas light rays 92 from the remaining uncovered areas 80 outside the covered area 76 reach the camera 24 without passing through the polarizing filter 40. This arrangement allows a single image of the can end 12 to be formed and processed in multiple ways, depending on the information presented in the image. For example, the image of the sealing material 74 in the center of the can end 12 can be processed based on the difference between the polarized light from the uncovered areas 80 and the unpolarized light from the covered areas 76. At the same time, the image of the periphery of the can end 12 can be processed in a manner that takes advantage of the properties of the second sealing material 84 by blocking out the center portion of the image with the first sealing material 74.

Figure 4:
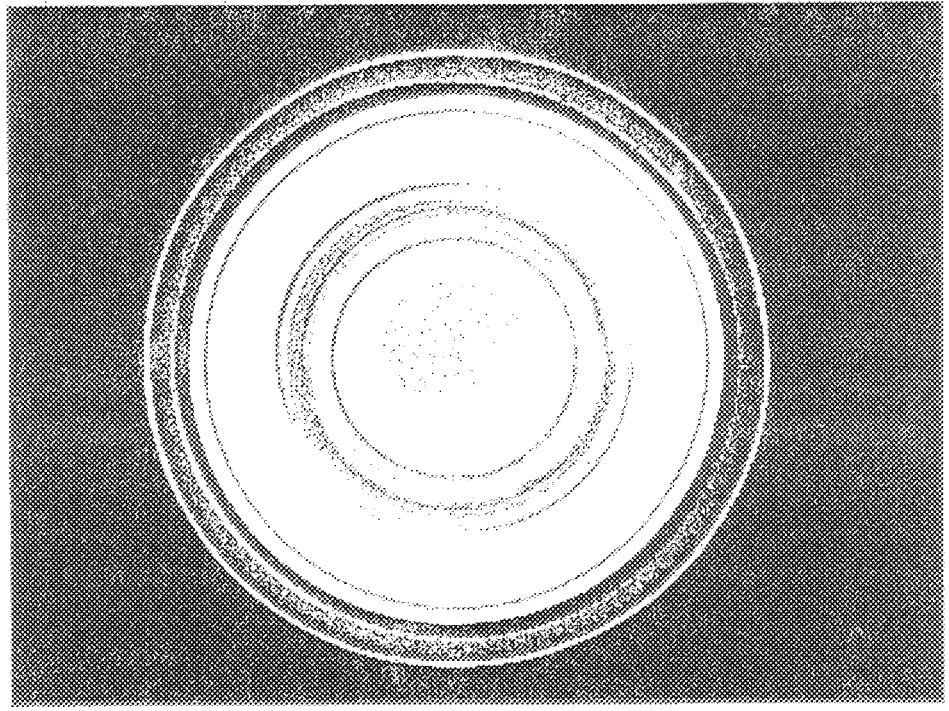
FIG. 4 is an image of an uneven reflection from a good part.
Figure 5:
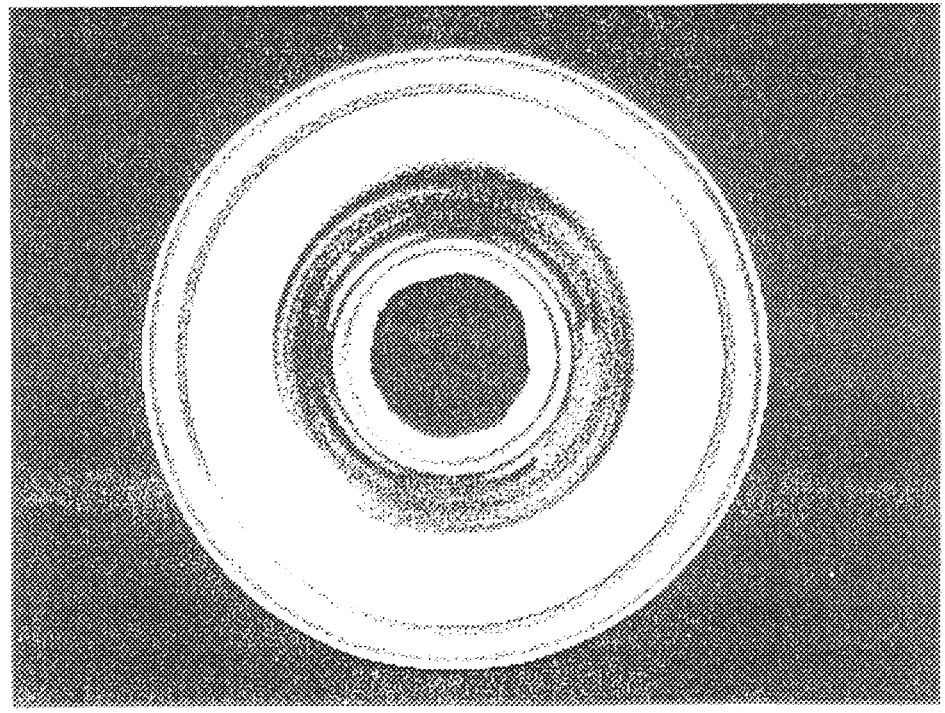
FIG. 5 is an image of the good part of FIG. 4 with polarized lighting reflections suppressed.

FIG. 4 is an image of a good part taken using unpolarized light. The light reflections are uneven, being washed out in portions of the critical coated areas 76. FIG. 5 shows an image of the same part shown in FIG. 4, but the image was taken using polarized light according to the present invention. The image of FIG. 5 shows the polarized light reflection being suppressed by the analyzer 18.

Figure 6:
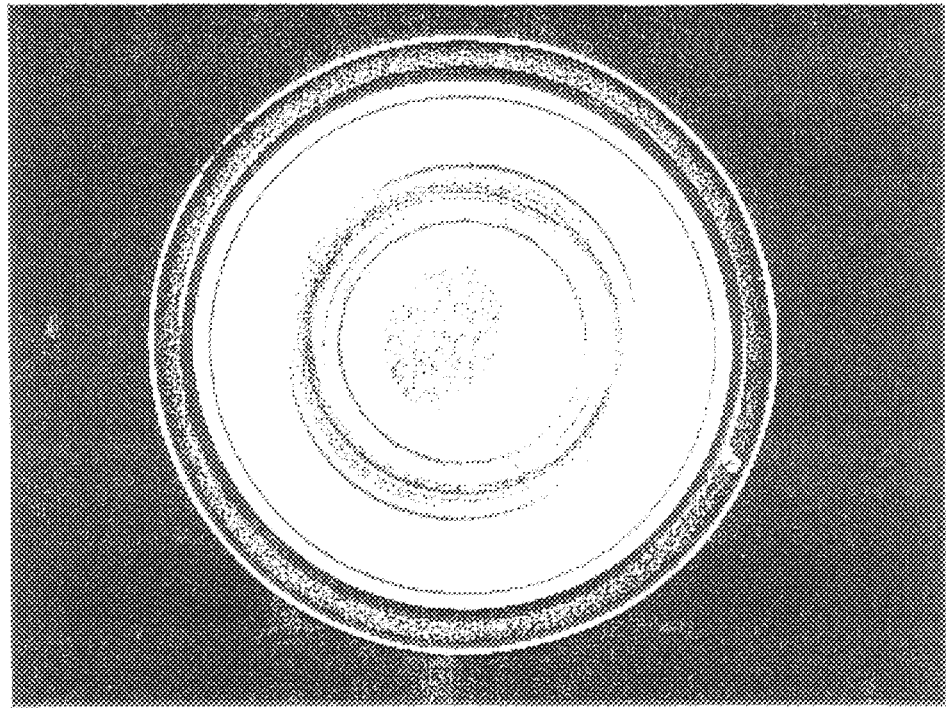
FIG. 6 is an image of an uneven reflection from a defective part inspected with nonpolarized lighting.
Figure 7:
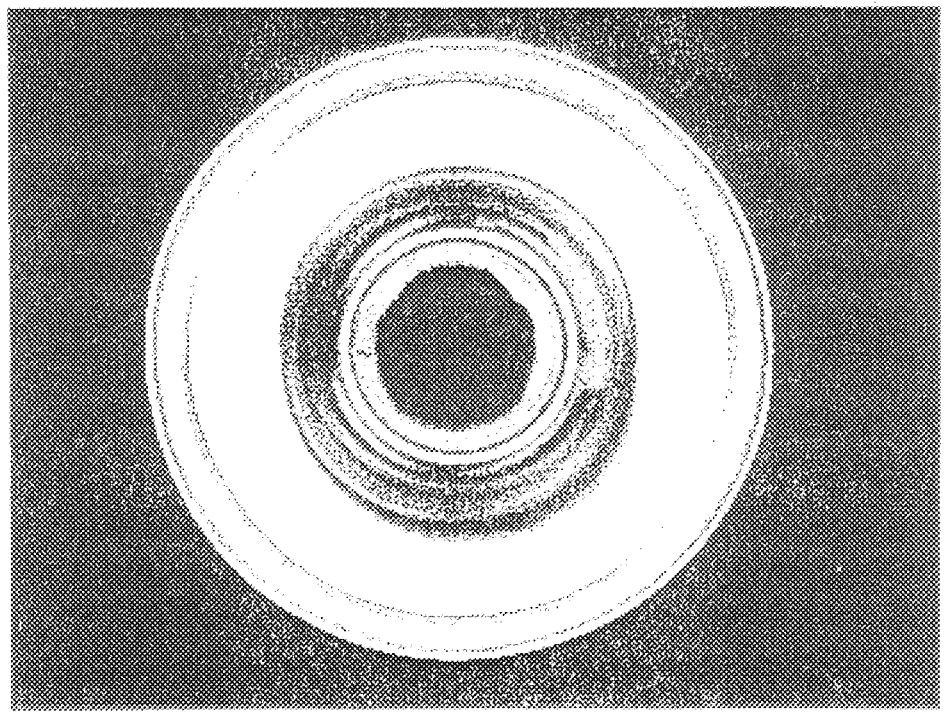
FIG. 7 is an image of the defective part of FIG. 6 with polarized lighting reflections suppressed.

FIG. 6 is an image of a defective part having a defect 96 in the covered area of the can end 12 using unpolarized light. In FIG. 6, the defect 96 is barely visible and could be erroneously ignored or missed by a defect detection system. As seen by the uneven reflections, the location of the defect relative to the image can have a dramatic effect on the detection capabilities of a detection system. For example, if the defect 96 was located on the opposite side of the can end 12, it would have been washed out entirely. The defect 96 is also imaged in FIG. 7 by polarized light according to the invention. However, in FIG. 7 the contrast between the defect 96 and the surrounding sealing material 74 is much more pronounced and therefore more detectable. The improved contrast allows the sensitivity of the detection system to be set to provide for fewer false rejections while minimizing the number of missed defects.

Although the invention has been described in detail with reference to a particular preferred embodiment, variations and modifications exist within the scope and spirit of the invention as described and defined in the following claims.

We claim:

1. A method for illuminating and imaging a can end having at least a portion thereof covered with a sealing material, the method comprising the steps of:

conveying the can end to an inspection station;

illuminating the can end with polarized light at the inspection station;

providing a polarizing filter and a camera at the inspection station;

positioning the polarizing filter between the camera and the can end so that light from the sealing material passes through the polarizing filter before reaching the camera; and orienting the polarizing filter to minimize the intensity of the polarized light received by the camera.

2. A method for illuminating and imaging a can end having at least a portion thereof covered with a sealing material, the method comprising steps of:

conveying the can end to an inspection station;

illuminating the can end with polarized light at the inspection station;

providing a polarizing filter and a camera at the inspection station;

positioning the polarizing filter between the camera and the can end so that light from the sealing material passes through the polarizing filter before reaching the camera; and moving the polarizing filter relative to the camera so as to substantially limit the light reaching the camera through the polarizing filter to light reflected from the covered portion of the can end.

3. The method of claim 2 further comprising the step of positioning the camera to include the entire can end within the field of view of the camera.

4. A method for detecting defects in a sealing material covering at least a portion of a can end, the method comprising the steps of:

conveying the can end to an inspection station;

illuminating the can end with polarized light;

passing light from the coated portion of the can through a polarizing filter; and orienting the polarizing filter to differentiate between light reflected from the covered portion and light reflected from any uncovered portions.

5. A method for detecting deflects in sealing material that coats at least a portion of a can end by forming a defect image, the method comprising the steps of:

conveying the can end to an inspection station;

illuminating the sealing material with polarized light;

passing light from sealing material through a polarizing filter; and orienting the polarizing filter to enhance the image of a defeat in the sealing material.

6. the method of claim 5 wherein the illuminating step includes the step of providing a light fixture and at least partially covering the light fixture with a polarizing sheet and preventing unpolarized light from illuminating the can end.

7. The method of claim 6 wherein the orienting step includes the step of positioning the polarizing filter between the can end and a camera to substantially limit the light received by the camera through the polarizing filter to the light reflected from the coated portion of the can end.

8. The method of claim 7 further including the step of positioning the camera to include the entire can end within the field of view of the camera.

9. An apparatus for illuminating and imaging a can end at least partially covered with sealing material, the apparatus comprising:

a light source for illuminating the can end;

a polarizer for polarizing the light illuminating the can end; and imaging means for receiving light reflected from the can end; and a polarizing filter positioned between the can end and the imaging means, said polarizing filter being oriented to increase the contract between light reflected from the covered portion of the can end and light reflected from uncovered portions of the can end.

10. The apparatus of claim 9 further including means for moving the polarizing filter relative to the imaging means to limit the area viewed by the imaging means through the polarizing filter to the covered portion of the can end.

11. The apparatus of claim 10 wherein the camera is positioned so that the field of view of the camera includes the entire can end.

12. An apparatus for illuminating and imaging a can end having a portion covered with sealing material, the apparatus comprising:

means for providing polarized light for illuminating the can end, said providing means comprising a light source for illuminating the can end and means for polarizing the light from the light source, said light source including a circular fluorescent light fixture disposed about the optical axis of the camera, said polarizing means including a polarizing sheet positioned relative to the fixture and configured to prevent unpolarized light from reaching the can end, a polarizing filter positioned between the can end and the camera and oriented to enhance the image of a defect in the sealing material; and means for moving polarizing filter relative to the camera to limit the light that reaches the camera through the filter to light reflected from the covered portion of the can end and any uncovered area enclosed by the covered portion.

13. An apparatus for illuminating and imaging a can end at least partially covered with sealing material, the apparatus comprising:

means for moving the can end to an inspection system;

a light source;

means, disposed between the light source and the can end, for polarizing the light from the light source;

a camera positioned to receive light reflected from the can end; and a polarizing filter, positioned between the can end and the camera, said polarizing filter being oriented to prevent polarized light reflected from the covered portion of the can end from being received by the camera and for enhancing the image of a defect in the sealing material.

14. The apparatus of claim 13 wherein the light source includes a circular fluorescent light fixture disposed about the optical axis of the camera.

15. The apparatus of claim 14 wherein the polarizing means includes a polarizing sheet positioned relative to the light fixture to prevent unpolarized light from illuminating the can end.

16. The apparatus of claim 13 further including means for positioning the camera relative to the can end to include the entire can end within the field of view of the camera.

* * * * *